(12) United States Patent
Pataut et al.

(10) Patent No.: US 6,177,066 B1
(45) Date of Patent: Jan. 23, 2001

(54) SOLID DEODORANT COMPOSITION

(75) Inventors: Françoise Pataut, Paris; Lionel Aubert, Domont, both of (FR)

(73) Assignee: L'Oreal, Paris (FR)

( * ) Notice: Under 35 U.S.C. 154(b), the term of this patent shall be extended for 0 days.

(21) Appl. No.: 09/274,879

(22) Filed: Mar. 23, 1999

(30) Foreign Application Priority Data

Mar. 23, 1998 (FR) .................................. 98 03539

(51) Int. Cl.$^7$ .............................. A61K 7/32; A61K 7/34; A61K 7/38
(52) U.S. Cl. ................. 424/65; 424/66; 424/68; 424/401
(58) Field of Search ............... 424/401, 65, 66, 424/68

(56) References Cited

U.S. PATENT DOCUMENTS

| | | | |
|---|---|---|---|
| 4,822,603 | 4/1989 | Farris et al. | 424/66 |
| 5,972,319 | * 10/1999 | Linn et al. | 424/65 |

FOREIGN PATENT DOCUMENTS

| | | |
|---|---|---|
| 1596791 | 8/1981 | (GB) . |
| 55-2678 | 1/1980 | (JP) . |
| 57-112315 | 7/1982 | (JP) . |
| 58-78662 | 5/1983 | (JP) . |
| 60-181011 | 9/1985 | (JP) . |
| 62-145013 | 6/1987 | (JP) . |
| 4-189352 | 7/1992 | (JP) . |

OTHER PUBLICATIONS

Cosmetic and Toiletry Formulations, Ernest W. Flick, pp. 28 and 29.*

Chemical Abstracts, vol. 104, No. 2, Jan. 13, 1986, No. 10407.

* cited by examiner

*Primary Examiner*—Thurman K. Wage
*Assistant Examiner*—Amy E Pulliam
(74) *Attorney, Agent, or Firm*—Jacobson, Price, Holman & Stern, PLLC

(57) ABSTRACT

The invention relates to a solid deodorant composition, which is essentially anhydrous and comprises, as a solidifying agent, a mixture of waxes containing at least one synthetic polyethylene wax having a melting point of greater than 80° C., and at least one wax of natural origin having a melting point of greater than 80° C., as well as at least one deodorant active principle and a process for reducing the flow of sweat, and for masking, improving or reducing the unpleasant smell resulting from the decomposition of human sweat by bacteria using said composition.

28 Claims, No Drawings

SOLID DEODORANT COMPOSITION

Anhydrous deodorant sticks have been known and used for many years. They offer many advantages with respect to other deodorant presentation forms, in particular with respect to aerosols. These advantages are, for example, high safety of use and storage, the absence of propellent gases harmful to the ozone layer, simple and economical packaging, and good stability on storage due to the absence of drying phenomena.

Use is conventionally made, as solidifying agent in anhydrous deodorant compositions, of a combination of two types of waxes, one having a relatively low melting point, namely of less than 80° C., and the other having a high melting point, that is to say of greater than 80° C.

The wax with a low melting point which is most commonly described in the literature and used in commercial products is stearyl alcohol, which has a melting point of 60° C.

The main disadvantages of the combination of a wax with a high melting point and of a wax with a low melting point, such as stearyl alcohol, are the brittleness of the bars of the sticks, reducing their durability, and the deposition on the skin of significant off-white traces which can subsequently be transferred to clothing.

The Applicant Company has now discovered that it is possible to overcome these disadvantages by using, as agent for solidifying anhydrous deodorant compositions, a mixture of waxes devoid of waxes with low melting points, that is to say a mixture composed solely of waxes all having melting points greater than 80° C.

The deodorant compositions of the present invention, solidified by such a combination of at least two waxes with high melting points, exhibit excellent durability on use and less whitening of the skin after application, while retaining their cosmetic qualities, in particular good properties on spreading, such as smoothness, slip and wear.

The subject-matter of the present invention is consequently a solid deodorant composition comprising, as solidifying agent, a mixture of waxes all having melting points of greater than 80° C., and at least one deodorant active principle.

More particularly, the mixture of waxes of the present invention comprises:

at least one synthetic polyethylene wax having a melting point of greater than 80° C., and at least one wax of natural origin having a melting point of greater than 80° C.

The polyethylene wax or waxes have the function of conferring on the product its necessary properties of spreading, of wear and of slip. The natural wax or waxes with high melting points, in combination with the first wax or waxes, strengthen the structure of the bar of the stick and contribute the stiffness necessary to avoid the disintegration of the sticks.

The polyethylene wax with a high melting point (>80° C.) used according to the invention is an ethylene homopolymer or a copolymer of ethylene and of another copolymerizable monomer corresponding to the following formula (I):

$$CH_2=CHR \qquad (I)$$

in which R represents a linear or branched alkyl chain which can be interrupted by mono-or polyoxyalkylene units, an aryl or aralkyl radical or —$CH_2COOH$ or —$CH_2CH_2OH$ radical.

The alkyl radicals more particularly denote the methyl, ethyl, propyl, isopropyl, decyl, dodecyl and octadecyl radicals.

The mono- or polyoxyalkylene units preferably denote mono- or polyoxyethylene groups or mono-or polyoxypropylene groups.

The aryl radical is preferably a phenyl or tolyl radical.

The aralkyl radical is, for example, a benzyl or phenethyl radical.

The weight-average molar mass of the polyethylene wax with a high melting point according to the invention is preferably between approximately 400 and 1000, more particularly between approximately 400 and 700 and is preferably about 500.

According to a preferred embodiment of the compositions according to the invention, the wax as defined above is chosen from ethylene homopolymers, copolymers of ethylene and of propylene, copolymers of ethylene and of maleic anhydride or acid, or oxidized or ethoxylated polyethylenes.

Mention may in particular be made, among the ethylene homopolymers which can be used according to the invention, of those sold under the names of Polywax 500, Polywax 655 and Polywax 1000 by the company Petrolite.

Mention may be made, among the ethylene copolymers which can be used according to the invention, of the copolymers of ethylene and of propylene sold under the names Petrolite® by the company Petrolite, the copolymers of ethylene and of maleic anhydride sold under the names Ceramer® by the company Petrolite, the oxidized polyethylenes sold under the names Unilin® and Unicid® by the company Petrolite, and the ethoxylated polyethylenes sold under the names Unithox® by the company Petrolite.

According to a particularly preferred embodiment of the invention, the polyethylene wax is an ethylene homopolymer wax.

In the anhydrous deodorant compositions of the present invention, the polyethylene wax as described above is used in combination with at least one second wax, which is a natural wax also having a melting point of greater than 80° C. This natural wax is chosen from mineral, fossil, animal or vegetable waxes, or hydrogenated oils, fatty esters, fatty alcohols or polyoxyethylenated fatty alcohols which are solid at 25° C.

Use may be made, as examples of waxes of natural origin in the deodorant compositions of the present invention, of microcrystalline waxes, ceresin, ozokerite, candelilla wax, carnauba wax, hydrogenated castor oil, hydrogenated palm oil or hydrogenated coconut oil.

According to a preferred embodiment of the invention, the natural wax is an ozokerite with a high melting point. Ozokerite is a fossil hydrocarbon with a complex composition corresponding to the solid residue from the evaporation of paraffin-rich petroleum.

A commercial ozokerite is the product Cerozo Blanche E626, a mixture of $C_{20-50}$ hydrocarbons sold by the company Barlocher.

The deodorant composition of the present invention comprises from 5 to 20% by weight of synthetic polyethylene wax and from 2 to 20% by weight of the said natural wax with a high melting point.

The proportion of polyethylene wax is preferably greater than that of the natural wax and the (polyethylene wax/natural wax) ratio by weight is in particular between 10/1 and 1/1 and especially between 7/1 and 3/1.

The deodorant composition of the present invention comprises, in addition to the mixture of waxes with high melting points, at least one deodorant active principle.

Within the meaning of the present invention, deodorant active principle is understood to mean any substance capable of reducing the flow of sweat and/or of masking, improving or reducing the unpleasant smell resulting from the decomposition of human sweat by bacteria.

It is, for example, an antiperspirant compound, such as aluminium and/or zirconium salts, for example an aluminium hydroxychloride or an aluminium and zirconium hydroxychloride, or alum salts, a bacteriostatic agent, a bactericidal agent, such as 2,4,4-trichloro-2-hydroxydiphenyl ether and 3,7,11-trimethyldodeca-2,5,10-trienol, and various zinc salts, an odour-absorbing agent, such as sodium bicarbonate, an antioxidizing agent, such as butylated hydroxytoluene, or a mixture of these compounds and/or agents. 3,7,11-Trimethyldodeca-2,5,10-trienol is, for example, sold under the name Farnesol® by the company Dragoco and 2,4,4-trichloro-2-hydroxydiphenyl ether under the name Irgacare® MP by the company Ciba-Geigy.

Mention may be made, among aluminium salts, of the product sold by the company Reheis under the name Reach 301 or by the company Guilini Chemie under the name Aloxicoll PF 40.

Aluminium and zirconium salts are, for example, that sold by the company Reheis under the name Reach A2P-908-SUF.

This deodorant active principle or mixture of deodorant active principles is present in a proportion of approximately 0.01 to 40% by weight with respect to the overall composition, preferably in a proportion of approximately 0.05 to 25% by weight.

When the deodorant active principle is an aluminium hydroxychloride or an aluminium and zirconium hydroxycloride, it is present in a proportion of 2 to 30% by weight, preferably in a proportion of 5 to 25% by weight, with respect to the total mass of the composition.

The solid deodorant composition of the present invention can additionally comprise one or more emollient agents. The function of these emollient agents is to improve the cosmetic properties of the final product, to promote good sliding of the bar of the stick over the skin and thus to facilitate the application of the deodorant composition. The emollient agents are, for example, volatile silicones, such as the product sold under the name DC246 Fluid by the company Dow Corning, and non-volatile silicones, such as, for example, the product DC556 sold by the company Dow Corning, polydecenes, such as the product Silkflo® S366 NF from the company Amoco, fatty acid esters, such as the product sold by the company Unichema under the name Estol® 1517, fatty alcohols, ethoxylated and/or propoxylated surface-active agents or polyalkoxylated esters of glycol or PPG(14) butyl ether (Fluide AP from the company Union Carbide).

The content of emollient agents in the composition of the present invention is generally between 10 and 70% by weight, preferably between 20 and 60% by weight.

In addition, the deodorant composition according to the invention generally comprises one or more fillers incorporated in the form of very fine particles in the fatty substance of the composition. These fillers are chosen, for example, from talc, silica, starch derivatives, clay or acrylate copolymers (Expansel 551 DE from the company Kemanord) and are generally present in a proportion of approximately 0.1 to 10% by weight with respect to the total mass of the composition.

In addition, the deodorant composition according to the invention can comprise other adjuvants, such as, for example, fragrances and/or colorants. Of course, a person skilled in the art will take care to choose this or these possible additional compounds so that the advantageous properties intrinsically attached to the deodorant composition in accordance with the invention are not, or not substantially, detrimentally affected by the envisaged addition or additions.

The solid deodorant composition of the invention is generally provided in the form of a deodorant stick.

Another subject-matter of the present invention is the use of the compositions described above for reducing the flow of sweat and/or for masking, improving or reducing the unpleasant smell resulting from the decomposition of human sweat by bacteria.

This use consists in applying, preferably daily, the solid deodorant composition to the clean skin parts which it is desired to treat, preferably under the armpits.

The non-limiting examples below illustrate the present invention.

EXAMPLES 1 AND 2 AND COMPARATIVE EXAMPLES A AND B

Four solid deodorant compositions 1, 2, A and B, presented in Table 1 below, are prepared which differ essentially in the nature of the solidifying agents used.

Compositions 1 and 2 are compositions in accordance with the present invention comprising, as solidifying agent, two waxes with melting points greater than 80° C. Compositions A and B are compositions corresponding to the state of the art comprising, as solidifying agent, a wax with a high melting point (>80° C.) and a wax with a low melting point (<80° C.), namely stearyl alcohol, which has a melting point of 60° C.

TABLE 1

| Ingredients (in parts by weight) | Composition 1 | Composition 2 | Composition A | Composition B |
|---|---|---|---|---|
| Ozokerite (Cerozo Blanche E626 ®) | 3.00 | 7.00 | | |
| Polyethylene wax (Polywax ® 500) | 14.00 | 10.00 | 10.00 | |
| Hydrogenated castor oil (Cutina ® HR) | | | | 5.00 |
| Stearyl alcohol | | | 7.00 | 17.50 |
| Polypropoxylated butyl alcohol (14 PO) | 10.00 | 10.00 | 10.00 | 10.00 |
| di-tert-Butyl-4-hydroxytoluene | 0.05 | 0.05 | 0.05 | 0.05 |
| Dow Corning 245 Fluid ® | 30.00 | 30.00 | 30.00 | 30.00 |
| Silkflo ® | 25.45 | 25.45 | 25.45 | 19.95 |
| Polyethylene glycol distearate (8 EO) | 2.50 | 2.50 | 2.50 | 2.50 |
| Aluminium and zirconium salt | 15.00 | 15.00 | 15.00 | 15.00 |

Cerozo Blanche E626® is a neutralized and protected $C_{20-50}$ hydrocarbon wax sold by the company Barcocher Polywax® 500 is a polyethylene wax with a molar mass of 500 sold by the company Petrolite Cutina® HR is hydrogenated castor oil sold by the company Henkel Dow Corning 245 Fluid® is a D5 silicone oil sold by the company Dow Corning Silkflo® is a hydrogenated polydecene with a molar mass equal to 549 sold by the company Amoco Each of these four deodorant compositions is subjected to two tests intended to evaluate:

1—their resistance to shearing

2—their static brittleness.

1—The shear test consists in measuring the maximum force (in g) exerted by a standard wire which a sample endures under defined conditions before being severed by this wire. This test is carried out by means of an electronic failure-measuring device designed by OREAL RAD and manufactured by the company J. Bouleffroy (Estrées Saint-Denis, France).

The sample to be tested is placed for at least 16 hours in a controlled chamber stabilized at 20±1° C. Immediately before the measurement, the sample is fitted into the cup holder, which is adjusted so that the distance between the wire and the bar of the stick is equal to 2–3 mm and that the wire is situated perpendicularly to the longitudinal axis of the stick at exactly 10 mm from the base (cup) of the latter. The minimum force (in g) necessary in order to sever the stick with the said standard wire is subsequently measured.

2—The static brittleness test consists in measuring the maximum force (in N) exerted by a standard tool (flat surface of a calliper) which a sample endures under defined conditions before being split by this tool. This test is also carried out using the failure-measuring device which has been used for measuring the resistance to shearing described above.

The sample to be tested is placed for at least 16 hours in a controlled chamber stabilized at 20±1° C. Immediately before the measurement, it is fitted into the cup holder, which is adjusted so that the cut face of the stick is parallel to the flat surface of the calliper at a distance of 3 mm from the latter. The minimum force (in N) necessary in order for the flat surface of the calliper, pressed against the cut face of the stick, to split the latter is subsequently measured.

The results of these tests, obtained for the two compositions of the invention (1 and 2) and the two comparative compositions (A and B), are shown in the following Table 2.

TABLE 2

|  | Composition 1 | Composition 2 | Composition A | Composition B |
|---|---|---|---|---|
| Resistance to shearing (in g) | 185 ± 5 | 154 ± 3 | 121 ± 4 | not measurable (stick disintegrated) |
| Static brittleness (in N) | 6.9 ± 1.1 | 5.7 ± 0.3 | 4.4 ± 0.2 | not measurable (stick disintegrated) |

The values obtained are the arithmetic means ± standard deviation, calculated from 10 measurements.

These results show that Compositions 1 and 2 according to the invention exhibit a resistance to shearing and a static brittleness which are significantly better than those of Compositions A and B, the latter of which is even too brittle for measurements to be possible.

What is claimed is:

1. Solid deodorant composition, which is essentially anhydrous and comprises, as a solidifying agent, a mixture of waxes all having melting points of greater than 80° C., and at most 40% by weight of at least one deodorant active principle.

2. Solid deodorant composition according to claim 1, wherein the mixture of waxes comprises:
   at least one synthetic polyethylene wax having a melting point of greater than 80° C., and
   at least one wax of natural origin having a melting point of greater than 80° C.

3. Solid deodorant composition according to claim 2, wherein the synthetic wax with a melting point of greater than 80° C. is an ethylene homopolymer or a copolymer of ethylene and of another copolymerizable monomer corresponding to the formula (I):

$$CH_2=CH-R \quad (I)$$

in which R represents a linear or branched alkyl chain which can be interrupted by mono-or polyoxyalkylene units, an aryl or aralkyl radical, or a $-CH_2COOH$ or $-CH_2CH_2OH$ radical.

4. Solid deodorant composition according to claim 3, wherein the ethylene homopolymer or copolymer wax has a weight-average molar weight of between 400 and 1000.

5. Solid deodorant composition according to claim 4, wherein the said wax is an ethylene homopolymer having a molar weight of approximately 500.

6. Solid deodorant composition according to claim 2, wherein the natural wax having a melting point of greater than 80° C. is selected from the group consisting of mineral, fossil, animal and vegetable waxes, hydrogenated oils, fatty esters, fatty alcohols and polyalkoxylated fatty alcohols which are solid at 25° C.

7. Solid deodorant composition according to claim 6, wherein the natural wax is selected from the group consisting of a microcrystalline wax, ceresin, ozokerite, candelilla wax, carnauba wax, hydrogenated castor oil, hydrogenated palm oil and hydrogenated coconut oil.

8. Solid deodorant composition according to claim 7, wherein the natural wax is ozokerite.

9. Solid deodorant composition according to claim 2, wherein the polyethylene-based wax is present in a proportion of 5 to 20% by weight with respect to the total weight of the composition.

10. Solid deodorant composition according to claim 2, wherein the natural wax is present in a proportion of 2 to 20% by weight with respect to the total weight of the composition.

11. Solid deodorant composition according to claim 2, wherein the synthetic polyethylene wax is present in a proportion greater than that of the natural wax.

12. Solid deodorant composition according to claim 11, wherein the ratio by weight of the synthetic wax to the natural wax is between 10/1 and 1/1.

13. Solid deodorant composition according to claim 1, wherein the deodorant active principle is present in a proportion of 0.01 to 40% by weight with respect to the total weight of the composition.

14. Solid deodorant composition according to claim 1, wherein the deodorant active principle is selected from the group consisting of aluminium salts, zirconium salts, aluminium and zirconium salts, alum salts, bacteriostatic agents, bactericidal agents, odour-absorbing substances and antioxidizing agents.

15. Solid deodorant composition according to claim 14, wherein the deodorant active principle is an aluminium hydroxychloride or an aluminium and zirconium hydroxychloride.

16. Solid deodorant composition according to claim 15, wherein the aluminium hydroxychloride or the aluminium and zirconium hydroxychloride is present in a proportion of 2 to 30% by weight with respect to the total weight of the composition.

17. Solid deodorant composition according to claim 1, which additionally comprises one or more emollient agents.

18. Solid deodorant composition according to claim 17, wherein the emollient agent is selected from the group consisting of volatile and non-volatile silicones, polydecenes, fatty acid esters, fatty alcohols, ethoxylated surface-active agents, propoxylated surface-active agents, ethoxylated and propoxylated surface-active agents, polyalkoxylated esters of glycol and polypropylene glycol (14) butyl ether.

19. Solid deodorant composition according to claim 18, wherein the emollient agent is present in a proportion of 10 to 70% by weight with respect to the total weight of the composition.

20. Solid deodorant composition according to claim 1, which additionally comprises one or more fillers.

21. Solid deodorant composition according to claim 20, wherein the filler is selected from the group consisting of talc, silica, starch derivatives, clay and acrylate copolymers.

22. Solid deodorant composition according to claim 21, wherein the filler is present in a proportion of 0.1 to 10% by weight with respect to the total weight of the composition.

23. Solid deodorant composition according to claim 1, which additionally comprises other adjuvants.

24. Solid deodorant composition according to claim 1, which is in the form of a stick.

25. Process for reducing the flow of sweat, and for masking, improving or reducing the unpleasant smell resulting from the decomposition of human sweat by bacteria, which comprises applying a solid composition according to claim 1 to the skin.

26. Solid deodorant composition according to claim 11, wherein the ratio by weight of the synthetic wax to the natural wax is between 7/1 and 3/1.

27. Solid deodorant composition according to claim 1, wherein the deodorant active principle is present in a proportion of 0.05 to 25% by weight with respect to the total weight of the composition.

28. Solid deodorant composition according to claim 15, wherein the aluminium hydroxychloride or the aluminium and zirconium hydroxychloride is present in a proportion of 5 to 25% by weight with respect to the total weight of the composition.

* * * * *